US011860321B2

(12) United States Patent
Miller et al.

(10) Patent No.: US 11,860,321 B2
(45) Date of Patent: Jan. 2, 2024

(54) RADIATION DOSE LATENCY MEASUREMENT SYSTEM

(71) Applicant: MODUS MEDICAL DEVICES INC., London (CA)

(72) Inventors: David John Munro Miller, London (CA); Nicholas Gerard Hartman, Parkhill (CA); Enzo Antonio Barberi, London (CA)

(73) Assignee: MODUS MEDICAL DEVICES INC., London (CA)

( * ) Notice: Subject to any disclaimer, the term of this patent is extended or adjusted under 35 U.S.C. 154(b) by 98 days.

(21) Appl. No.: 17/508,377

(22) Filed: Oct. 22, 2021

(65) Prior Publication Data

US 2022/0128714 A1    Apr. 28, 2022

Related U.S. Application Data

(60) Provisional application No. 63/094,976, filed on Oct. 22, 2020.

(51) Int. Cl.
  *G01T 1/185* (2006.01)
  *G01T 1/02* (2006.01)
  *A61N 5/10* (2006.01)

(52) U.S. Cl.
  CPC ............ *G01T 1/185* (2013.01); *A61N 5/1071* (2013.01); *A61N 5/1075* (2013.01); *G01T 1/02* (2013.01); *A61N 2005/1076* (2013.01)

(58) Field of Classification Search
  CPC ................. A61N 5/1071; A61N 5/1075; A61N 2005/1076; G01T 1/02; G01T 1/185
  See application file for complete search history.

(56) References Cited

U.S. PATENT DOCUMENTS

| 4,591,984 A | * | 5/1986 | Mori | ......................... G01T 1/15 |
| | | | | 250/363.02 |
| 4,751,390 A | * | 6/1988 | Kopp | ..................... G01T 1/026 |
| | | | | 250/370.06 |

(Continued)

FOREIGN PATENT DOCUMENTS

| CN | 103126695 B | 9/2016 |
| EP | 2837330 B1 | 10/2018 |

(Continued)

OTHER PUBLICATIONS

CIRS, Tissue Simulation & Phantom Technology, Press Contact, CIRS Releases MR Safe MRgRT Motion Management QA Phantom, Computerized Imaging Reference Systems, Inc., Norfolk, Va (Apr. 22, 2019).

(Continued)

*Primary Examiner* — Blake C Riddick

(57) ABSTRACT

A radiation latency measurement system, having a pulse detector connected to a radiation detector mounted within a phantom that is configured to be positioned within a radiation treatment system which delivers a radiation dose to the radiation detector. The pulse detector has a first circuit that applies a high voltage bias to the radiation detector and a second circuit that amplifies the voltage signal from the radiation detector with a fixed gain first amplification stage and a variable gain second amplification stage. A first comparator receives the amplified signal and generates an output signal when the amplified signal exceeds a specified voltage level and a second comparator that processes and filters the output signal. The timing of receipt of the radiation dose signal may be compared to the position of the radiation detector in order to measure a radiation dose latency of the radiation treatment system.

13 Claims, 5 Drawing Sheets

(56) References Cited

U.S. PATENT DOCUMENTS

| | | | |
|---|---|---|---|
| 6,240,162 B1* | 5/2001 | Hernandez-Guerra | A61N 5/1048 378/65 |
| 8,042,209 B2 | 10/2011 | D'Souza et al. | |
| 8,239,005 B2 | 8/2012 | Wright et al. | |
| 2011/0006212 A1* | 1/2011 | Shchory | A61B 6/4258 378/65 |
| 2019/0022412 A1 | 1/2019 | Vertatschitsch et al. | |
| 2020/0346041 A1* | 11/2020 | Krishnaswamy | A61N 5/1045 |
| 2021/0052186 A1* | 2/2021 | Mickevicius | A61B 5/055 |

FOREIGN PATENT DOCUMENTS

| | | | |
|---|---|---|---|
| EP | 3272395 B1 | 7/2019 | |
| JP | 5023057 B2 | 6/2012 | |
| JP | 5975733 B2 | 7/2016 | |
| WO | WO-2018161125 A1* | 9/2018 | A61N 5/1075 |

OTHER PUBLICATIONS

Wiley, Radiation Oncology Physics, Clinical Experience of MRI QUASAR motion phantom for latency measurements in 0.35T MR-LINAC, Jun. 2, 2020, Department of Radiation Oncology, DOI: 10.1002/ACM2.13118.

Sun Nuclear, ZEUS: MRgRT Motion Management QA Phantom—CIRS, Nov. 1, 2022, www.cirsinc.com/products/radiation-therapy/mrgrt-motion-managment-qa-phantom/.

\* cited by examiner

RADIATION DOSE LATENCY MEASUREMENT SYSTEM

FIELD OF THE INVENTION

The present invention relates to radiation dose measurement equipment, in particular, to a system to measure the timing (beam latency) of radiation dose delivery by a motion-gated Linac system.

BACKGROUND

Medical linear accelerators are used to deliver therapeutic doses of radiation to targeted structures within a patient. Software based radiotherapy planning systems are used to plan the radiation beams necessary to meet the clinically prescribed dose. This includes ensuring sufficient dose to the target, while maintaining minimal acceptable doses to surrounding tissues that are at risk of radiation damage (organs at risk, OAR).

Radiation plans are prepared using medical images (commonly, MM, CT, PET, or ultrasound) of the patient to be treated. Target and OAR structures are identified and plans are optimized using a variety of techniques and software-based optimization methods.

Some targets and OARs move during imaging and treatment, due to respiratory, cardiac, peristaltic, or other physiological motion. In order to optimize plans for these moving structures, some linear accelerators incorporate systems which enable motion management, including gating and breath-hold techniques. These gated systems may use external motion surrogates such as real time chest wall or abdominal wall position tracking, lung air displacement, or more recently, real time imaging of the internal structures of the patient.

The process of image based gating of the delivery of radiation requires the imaging system to acquire updated images in real time at 4 or more frames per second, combined with edge detection and motion tracking techniques to automate beam gating. Typically this is done with 1 or 2 dimensional images of the region including the target, but more recently, may include 3D and 4D deformable images. Software is used to determine the location of the important structures in the images (such as targets and OARs). These locations are then compared to the location required by the plan, within a margin or tolerance. The beam is either turned on or off, depending on whether the structures are in the required location or not, respectively.

As structures move, they may exit or enter the required location. As they exit the location, the beam is turned off. However, there is a delay (latency) caused by the time required for image acquisition, image processing, and the generation of the signal to turn off the beam, plus the time required for the linac to stop emitting radiation. This exit latency time represents time that the structures are out of position and radiation is still being delivered. This leads to undesirable radiation dose being delivered to healthy tissue, organs at risk, and arteries and blood vessels, resulting in dose toxicity, patient suffering and discomfort, and poorer patient outcomes. Similarly, there is a latency to turning the beam on. Beam on latency is less damaging to the patient, but any delay represents a reduction in the planned dose delivered to the intended target and inefficient use of the treatment equipment.

Latency timing is variable due to the asynchronous nature of each of the steps in the process. Medical physicists, responsible for the commissioning and ongoing quality assurance of the treatment equipment, require accurate measurement of beam latency, since it can affect patient outcomes.

Accordingly, there is a need for test phantoms that can accurately compare beam on and beam off times relative to accurately placed moving and stationary imaging targets.

SUMMARY OF THE INVENTION

A radiation latency measurement system, according to the present invention, has a pulse detector connected to a radiation detector mounted within a phantom that is configured to be positioned within a radiation treatment system which delivers a radiation dose to the radiation detector. The pulse detector receives and converts the small electrical currents produced from the radiation detector to an amplified voltage signal that can be used to determine the radiation dose latency of the treatment system independently from the treatment system, itself.

In another embodiment, the phantom is a motion phantom having a stationary portion and a moving portion with a control box that controls the movement of the moving portion of the phantom. The amplified voltage signal from the pulse detector may be compared by the control box with the known position of the radiation detector to determine the radiation dose latency of the treatment system.

In another embodiment, the pulse detector has a current amplifier to amplify the small electrical currents from the radiation detector, a first comparator to filter dose pulse signals from background noise, and a second comparator to extend the dose pulse signals so that they may be read by the control box or other radiation dose detector.

BRIEF DESCRIPTION OF THE DRAWINGS

In order that the invention may be more clearly understood, a preferred embodiment thereof will now be described in detail by way of example, with reference to the accompanying drawings, in which.

DESCRIPTION OF THE INVENTION

The radiation latency measurement system, according to present invention, measures the actual timing of delivery of a radiation dose to a target structure inside a Linac. This facilitates accurate quantification of the latency to verify and improve the accuracy of dose delivery to moving targets in gated radiation treatment programs.

Figure 1:
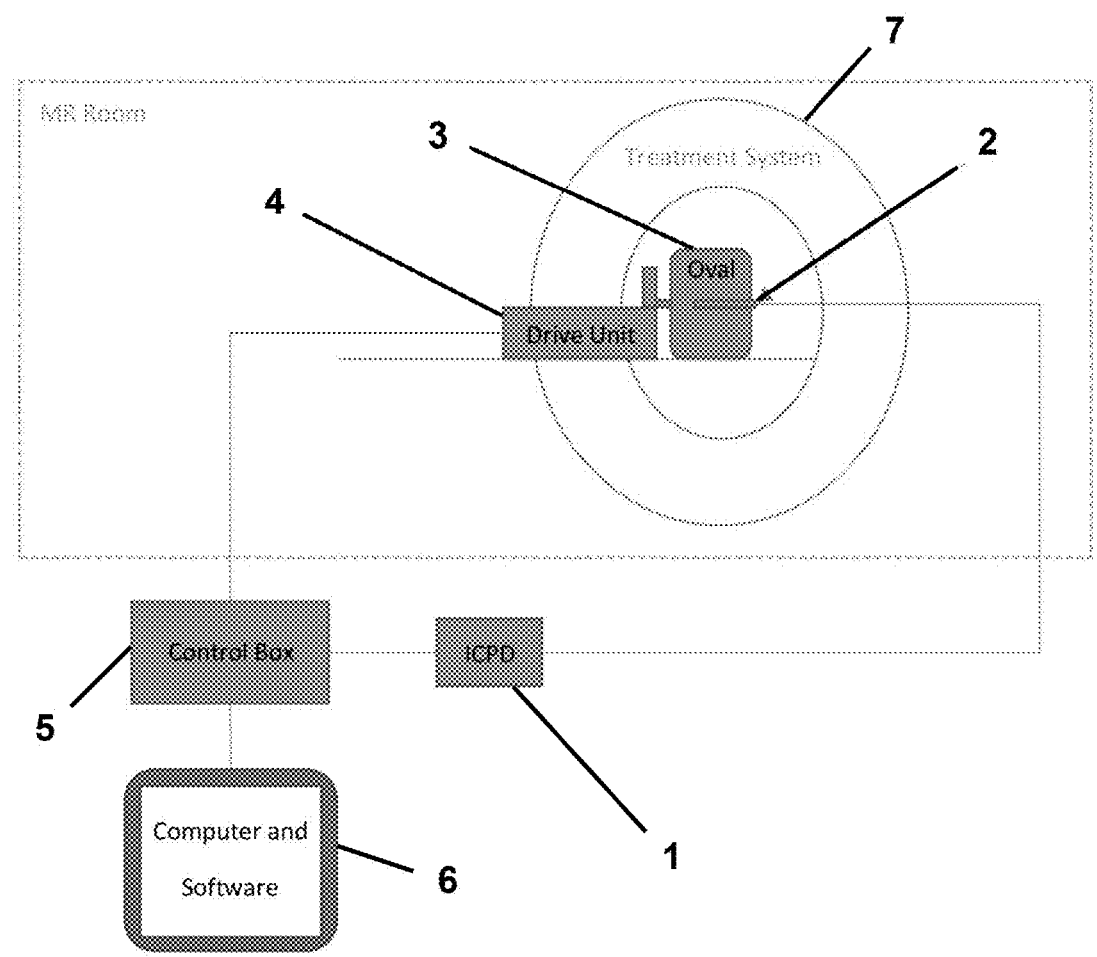
FIG. 1 is a schematic diagram of a radiation latency measurement system, according to the present invention, positioned for use in a radiation treatment system.

As shown in FIG. 1, the system has a pulse detector 1 connected to an ion chamber 2 mounted within a phantom 3. The phantom 3 is, preferably, a motion phantom with a drive unit 4 that drives the movement, in one or more dimensions, of at least a portion of the phantom 3. The drive unit 4 is connected to a control box 5, which precisely controls the position of the moving portion of the phantom 3. The control box 5 is connected to a computer 6 running phantom positioning software. Preferably, the pulse detector 1 is connected to the control box 5, which receives the signal from the pulse detector 1 when radiation strikes the ion chamber 2. Alternatively, the pulse detector 1 may be connected to the same computer 6 as the control box 5 or another computer.

The phantom 3 may be any type of radiation-compatible phantom, such as the Quasar™ MRI4D motion phantom manufactured by Modus QA™. The phantom 3, including the ion chamber 2, are placed within a treatment system 7, such as a MR-Linac radiation treatment system, which is configured to target the ion chamber 2 with a radiation dose. The phantom 3 and the drive unit 4 provide an anatomically analogous structure that simulates physiological motion of the target, in this case, the moving ion chamber 2. The ion chamber 2 may be provided with visible imaging structures to register the isocenter of the ion chamber 2. The treatment system 7 targets the ion chamber 2 as it moves in and out of the treatment planning volume, as defined by the treatment plan. The control box 5 provides real-time accurate position information of the ion chamber 2 to the computer 6, which can be compared with the signal sent from the pulse detector 1 to determine the lag time, or latency, between the time when the ion chamber 2 moves in or out of the treatment planning volume and the time when the radiation dose is actually delivered to the ion chamber 2 by the treatment system 7 or no longer detected by the ion chamber 2. This requires setting the control box 5 target position boundaries to coincide with the planning volume boundaries and may be adjusted by the end-user, as required for different planning volumes.

Figure 2A:
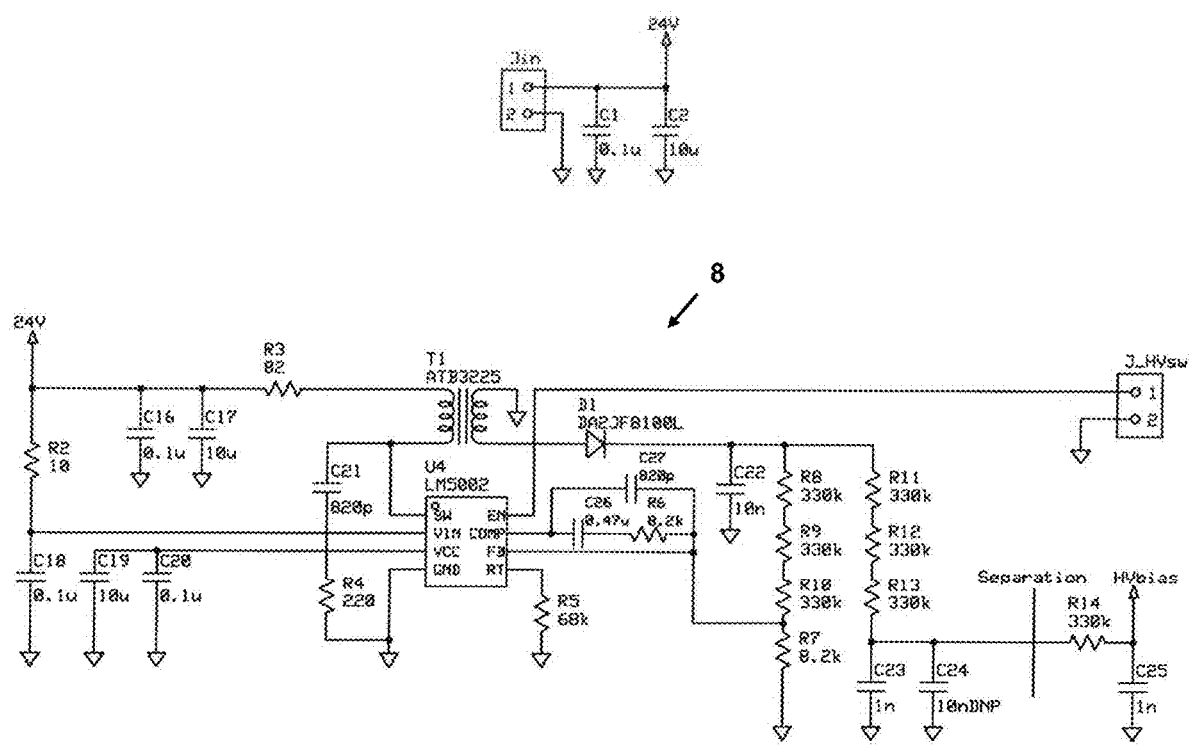
FIG. 2A is an electronic circuit schematic diagram of the high voltage power supply, of the pulse detector of the system of FIG. 1.
Figure 2B:
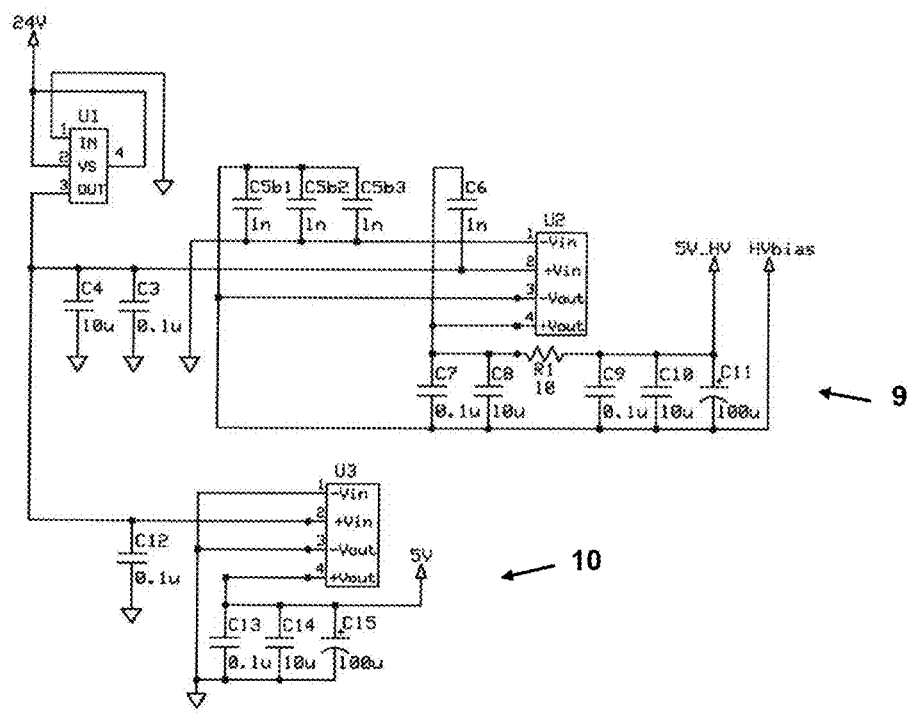
FIG. 2B is an electronic circuit schematic diagram of the high side and low side 5V power supplies of the pulse detector system of FIG. 1.
Figure 3A:
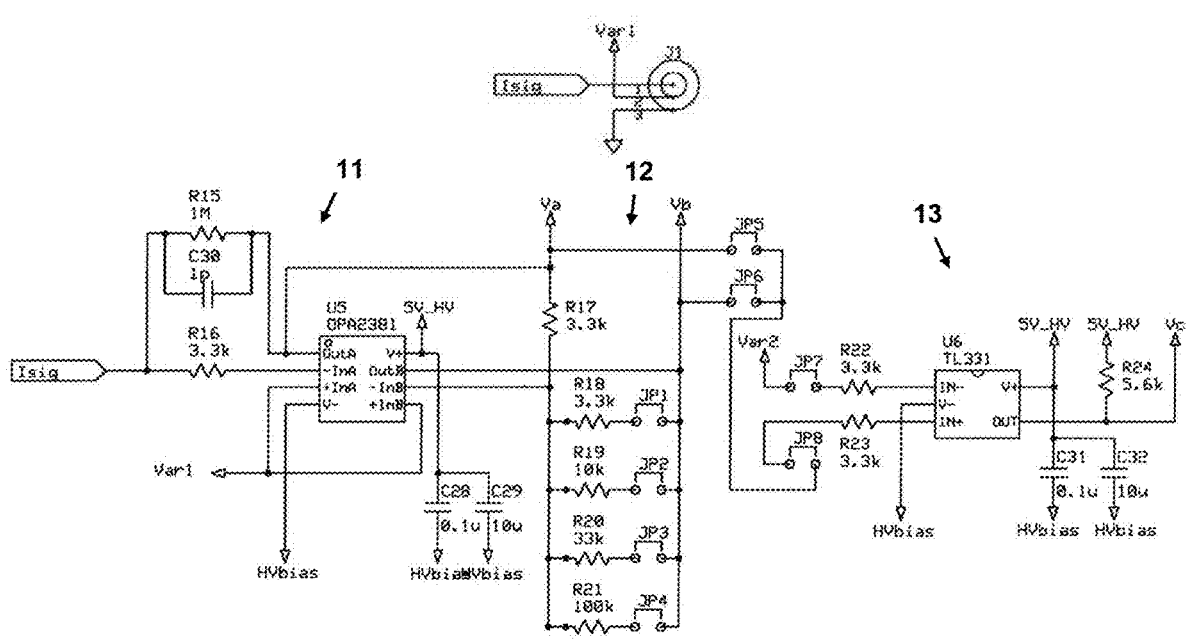
FIG. 3A is an electronic circuit schematic diagram of the current amplifier, gain select circuit, and a first comparator circuit of the pulse detector of the system of FIG. 1.
Figure 3B:
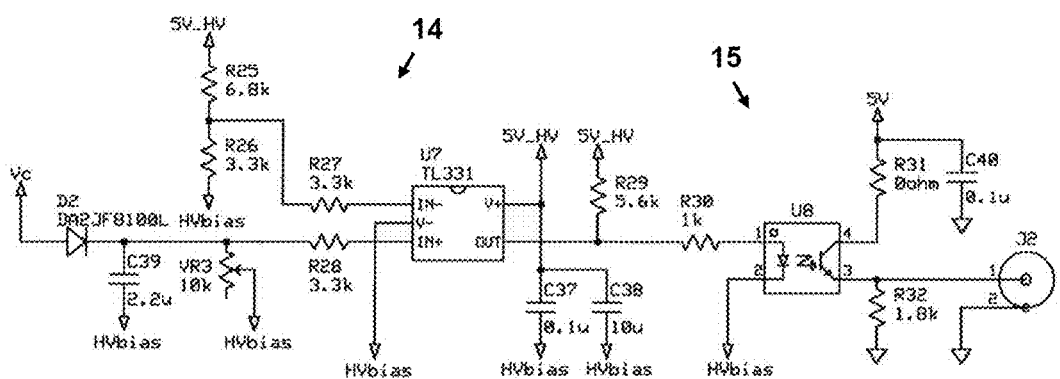
FIG. 3B is an electronic circuit schematic diagram of the second comparator circuit and a high side isolation circuit of the pulse detector of the system of FIG. 1.
Figure 3C:
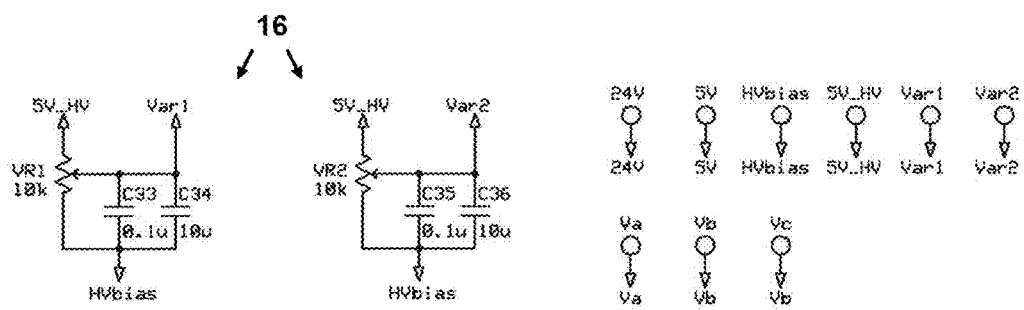
FIG. 3C is an electronic circuit schematic diagram of the offset adjustment circuits of the pulse detector of the system of FIG. 1.

In order to read the radiation dose signal from the ion chamber 2 and transmit it to the control box 5 or computer 6, the pulse detector 1 has an electronic circuit, preferably, as shown in FIGS. 2 and 3, that applies a high voltage bias to the ion chamber 2. When radiation is applied to the ion chamber 2, the circuit converts the small electrical currents produced from the ion chamber 2 to an amplified voltage signal. The amplification of the voltage signal from the ion chamber 2 has a fixed gain first amplification stage and a variable gain second amplification stage. The first amplification stage has a fixed gain to maintain a low noise amplification. The voltage signal is then further amplified to the required voltage range for detection in the second amplification stage, using a variable gain to support variations in ion chambers and Linac dose outputs, before being processed to meet the needs of the particular readout device, which is preferably the control box 5. The resulting voltage signal representing the dose pulses that are received from the ion chamber 2 is then outputted from the pulse detector 1 to the control box 5 or computer 6.

An exemplary circuit, as shown in FIG. 2, has a high voltage power supply 8, a high side 5V power supply 9, and a low side 5V power supply 10. The high voltage power supply 8 is connected to apply the high voltage bias to the ion chamber 2, while the high side 5V power supply 9 powers the signal amplification and processing circuits (described below) and the low side 5V power supply 10 powers the output to the control box 5 or computer 6.

As shown in FIG. 3, the electrical currents produced from the ion chamber 2, as it is subjected to radiation by the treatment system 7, are received and amplified by a current amplifier 11, which is connected to a gain select circuit 12 and a first comparator circuit 13 to amplify the small electrical currents produced by the ion chamber 2. The gain select circuit 12 provides a coarse adjustment in amplification to compensate for variations in ion chamber 2 collection efficiencies (i.e. between different models of ion chamber) and variations in Linac dose output. The first comparator circuit 13 provides an output signal such that when the amplified signal exceeds a specified voltage level, a dose pulse is detected.

The amplified output signal is then sent to a second comparator circuit 14 and a high side isolation circuit 15. The second comparator circuit 14 functions as a pulse extender to process and filter the output signal such that it meets the needs of the measurement device. For example, the dose pulses applied by many treatment systems 7 create detected dose pulse signals from the ion chamber 2 with too short a duration to be detected by many measurement devices. In order to address this problem, the dose pulse duration of the output signal is extended by the second comparator circuit 14 so that the measurement device, preferably the control box 5, is able to read the output signal. The high side isolation circuit 15 transfers the signal from being referenced to the high voltage to being referenced to the output ground, to ensure the signal is outputted with a safe voltage range, and transmits the output signal to either the control box 5 or the computer 6.

Offset adjustment circuits 16 are connected to the first and second comparator circuits 13 and 14 to set their respective voltage levels. The Offset adjustment circuits 16 provide a more granular adjustment for specifying the voltage level that identifies when a dose pulse has occurred.

Preferably, the output signal from the pulse detector 1 is sent to the control box 5, where it is compared with the known position of the ion chamber 2, based on the motion profile run by the control box 5. The signal timing can then be compared directly with the position of the ion chamber 2 in real time to determine the latency, or the time delay between the ion chamber 2 entering or exiting the treatment location and the radiation beam striking the ion chamber 2.

By connecting the pulse detector 1 to the control box 5 of a phantom 3, such as the Quasar™ MRI4D motion phantom manufactured by Modus QA™, a semi-automated system can be set up to measure the latency of a treatment system 7, without needing to interface with the treatment system 7. This is advantageous because vendors of radiation treatment systems, such as Linac systems, generally do not provide standardized outputs for performing gating latency measurements. The present invention thereby provides a radiation dose latency measurement system that may be used with any radiation treatment system 7 (i.e. across vendors) with the same setup. It also provides an independent latency measurement system that does not rely on information from the treatment system 7, itself.

Alternatively, the position information from the control box 5 and the radiation dose signal from the pulse detector 1 can be delivered separately to the computer 6 (or another system) for comparison to determine the latency. The pulse detector 1 may also be connected to other measurement equipment, such as an oscilloscope, to perform latency measurements manually.

The invention is described herein with reference to an ion chamber 2 as the radiation target and detector, but other suitable radiation detection devices may also be used. For example, diode detectors and detector arrays may be used in place of an ion chamber with only minor changes in the circuitry of the pulse detector 1 for 2D, 3D, and 4D measurements. Similarly, the phantom 3 may be another kind of motion phantom, provided that it is compatible with the treatment system 7 and provides accurate positioning and motion of the ion chamber 2 (or other radiation detector). Alternatively, simple latency measurements of the treatment system 7 may be made using a static phantom, where the ion chamber 2 is positioned in the target location within the treatment system 7. This may be useful, for example to simply verify the actual time delay between the radiation treatment "on" signal to the treatment system 7 and the radiation dose delivery to the ion chamber 2. Additionally, rigid or deformable radiosensitive gels could be placed in a moving insert in the phantom 3 to qualitatively measure latency, for example, through the observation of the dose penumbra dimensions, which grow with increased latency, and to quantitatively measure dose painting and accumulation in 3D and 4D.

The present invention has been described and illustrated with reference to an exemplary embodiment, however, it will be understood by those skilled in the art that various changes may be made and equivalents may be substituted for elements thereof without departing from the scope of the following claims. Therefore, it is intended that the invention not be limited to the particular embodiments disclosed herein.

What is claimed is:

1. A radiation latency measurement system, comprising a pulse detector connected to a radiation detector mounted within a phantom that is configured to be positioned within a particle accelerator which delivers a radiation dose to the radiation detector,
    wherein the phantom is a motion phantom having a stationary portion and a moving portion with a control box that controls the movement of the moving portion of the phantom,
    wherein the pulse detector is configured to send a radiation dose signal to the control box or a computer when the radiation detector receives the radiation dose from the particle accelerator, and
    wherein the control box or the computer compares the timing of receipt of the radiation dose signal to a position of the moving portion of the phantom in order to measure a radiation dose latency of the particle accelerator.

2. The radiation latency measurement system of claim 1, wherein the pulse detector comprises a first circuit that applies a high voltage bias to the radiation detector and a second circuit that amplifies the voltage signal from the radiation detector.

3. The radiation latency measurement system of claim 2, wherein the second circuit comprises a fixed gain first amplification stage and a variable gain second amplification stage.

4. The radiation latency measurement system of claim 2, wherein the second circuit comprises a current amplifier and a gain select circuit that receive the voltage signal from the radiation detector and produce an amplified signal, and a first comparator that receives the amplified signal and generates an output signal when the amplified signal exceeds a specified voltage level.

5. The radiation latency measurement system of claim 4, wherein the second circuit comprises a second comparator that processes and filters the output signal.

6. The radiation latency measurement system of claim 5, wherein the second comparator acts as a pulse extender to extend the duration of the output signal from the first comparator.

7. The radiation latency measurement system of claim 5, wherein the second circuit comprises a high side isolation circuit that reduces the voltage of the output signal to a safe voltage range.

8. The radiation latency measurement system of claim 5, wherein an offset adjustment circuit is connected to the first comparator circuit to permit adjustment of the specified voltage level for the first comparator circuit to generate the output signal.

9. The radiation latency measurement system of claim 1, wherein the pulse detector is configured to send a radiation dose signal to the control box when the radiation detector receives the radiation dose from the particle accelerator.

10. The radiation latency measurement system of claim 9, wherein the control box compares the timing of receipt of the radiation dose signal to the position of the moving portion of the phantom in order to measure the radiation dose latency of the particle accelerator.

11. The radiation latency measurement system of claim 10, wherein the radiation detector is an ion chamber.

12. The radiation latency measurement system of claim 10, wherein the radiation detector is mounted within the moving portion of the phantom.

13. The radiation latency measurement system of claim 10, wherein the radiation detector is mounted within the stationary portion of the phantom.

* * * * *